United States Patent [19]

Traxler et al.

[11] Patent Number: 5,686,457
[45] Date of Patent: Nov. 11, 1997

[54] PYRROLOPYRIMIDINE DERIVATIVES HAVING PHARMACOLOGICAL ACTIVITY

[75] Inventors: Peter Traxler, Schönenbuch, Switzerland; Pascal Furet, Thann, France; Wolfgang K.-D. Brill, Schopfheim, Germany

[73] Assignee: Novartis Corporation, Summit, N.J.

[21] Appl. No.: 434,419

[22] Filed: May 3, 1995

[30] Foreign Application Priority Data

May 3, 1994 [CH] Switzerland ............................ 1385/94
Jan. 30, 1995 [CH] Switzerland ............................ 245/95

[51] Int. Cl.$^6$ .................. A61K 31/505; C07D 403/02
[52] U.S. Cl. ........................ 514/258; 514/267; 544/280; 544/250
[58] Field of Search ......................... 544/280, 250; 514/258, 267

[56] References Cited

U.S. PATENT DOCUMENTS

| 3,037,980 | 6/1962 | Hitchings et al. | 514/258 |
| 3,311,628 | 3/1967 | Partyka | 514/258 |
| 3,631,045 | 12/1971 | Kim et al. | 514/258 |
| 4,229,453 | 10/1980 | Roth et al. | 544/280 |
| 5,034,393 | 7/1991 | Hackler et al. | 514/258 |
| 5,256,650 | 10/1993 | Peet et al. | 514/248 |
| 5,350,749 | 9/1994 | Hackler et al. | 514/248 |
| 5,496,822 | 3/1996 | Akimoto et al. | 514/258 |

FOREIGN PATENT DOCUMENTS

| 0475411 | 3/1992 | European Pat. Off. |
| 0566226 | 10/1993 | European Pat. Off. |
| 0602851 | 6/1994 | European Pat. Off. |
| 3036390 | 5/1982 | Germany |
| 63-107966 | 5/1988 | Japan |
| 41416491 | 5/1992 | Japan |
| 980515 | 1/1965 | United Kingdom |
| 9220642 | 11/1992 | WIPO |
| 9413676 | 6/1994 | WIPO |
| 9417803 | 8/1994 | WIPO |
| 9519774 | 7/1995 | WIPO |
| 9519970 | 7/1995 | WIPO |

OTHER PUBLICATIONS

Jorgensen, et al. "Phosphorus Pentoxide in Organic Synthesis, XX [1] Synthesis of N–Aryl–7H–pyrrolo [2,3–d] pyrimidin–4–amines." J. Heterocyclic Chem. 22:859 (1985).

Jorgensen et al. "Phosphorus Pentoxide in Organic Synthesis, XII Synthesis of 7H–Pyrrolo [2,3–d] pyrimidin–4–amines" Liebigs Ann. Chem: 142–148 (1985).

Girgis et al. "Phosphorus Pentoxide in Organic Synthesis; XI: A New Synthetic Approach to 7–Deazahypoxanthines" Synthesis (1): 101–104 (1985).

Girgis et al., Liebigs Ann. Chem. (1983) 2066–2072.

Jorgenson et al "Phosphorus Pentoxide in Organic Synthesis" Chem. Scripta 25, 222–226. (1985).

Marquet et al., Chimie Thérapeutique 6, 427–438 (1971).

*Primary Examiner*—Matthew V. Grumbling
*Attorney, Agent, or Firm*—Gregory D. Ferraro

[57] ABSTRACT

The invention relates to the use of the compounds mentioned below in the therapeutic treatment of tumour diseases and other proliferative diseases, such as psoriasis, and to novel compounds of that type. The compounds are compounds of formula I

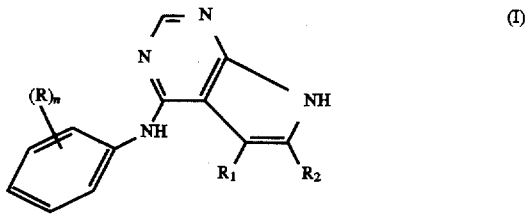

wherein n is from 0 to 5 and, when n is not 0, R is one or more substituents selected from halogen, alkyl, trifluoromethyl and alkoxy; and $R_1$ and $R_2$ are each independently of the other alkyl, or phenyl that is unsubstituted or substituted by halogen, trifluoromethyl, alkyl or by alkoxy, it also being possible for one of the two radicals $R_1$ and $R_2$ to be hydrogen, or $R_1$ and $R_2$ together form an alkylene chain having from 2 to 5 carbon atoms that is unsubstituted or substituted by alkyl; or salts thereof. Compounds of formula I inhibit protein kinases, for example the tyrosine protein kinase of the receptor for the epidermal growth factor, EGF.

2 Claims, No Drawings

PYRROLOPYRIMIDINE DERIVATIVES HAVING PHARMACOLOGICAL ACTIVITY

SUMMARY DESCRIPTION OF THE INVENTION

The present invention relates to a novel use of pyrrolopyrimidines, as such or in the form of pharmaceutical compositions, against particular diseases, to processes for the preparation of pharmaceutical compositions having the novel intended use, to pharmaceutical compositions comprising the pyrrolopyrimidines and to novel intermediates; the invention relates also to novel compounds of that type, to those novel compounds for use in a method for the diagnostic or therapeutic treatment of the human or animal body, and to processes for the preparation of those compounds.

BACKGROUND OF THE INVENTION

Since tumour diseases are one of the main causes of death in the industrial nations, very great efforts are being made to make available effective ways and means of treating tumours. In particular, because of the large number and wide variety of possible tumour diseases, there is a constant need for new pharmaceutical compounds and compositions which, by virtue of their active ingredients, are suitable either for treating as many tumours as possible or, alternatively, for treating very specific tumours.

Surprisingly, it has now been found that the compounds mentioned hereinafter are suitable for the therapeutic treatment of tumour diseases and other proliferative diseases, such as psoriasis, as well as of other diseases which are described in greater detail below.

FULL DESCRIPTION OF THE INVENTION

The compounds that can be used in accordance with the invention are compounds of formula I

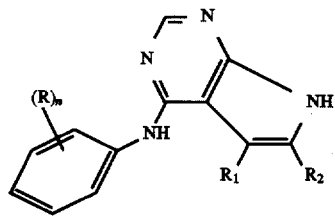

wherein n is from 0 to 5 and

R is a substituent selected from halogen, alkyl, trifluoromethyl and alkoxy; and $R_1$ and $R_2$ are each independently of the other alkyl, or phenyl that is unsubstituted or substituted by halogen, trifluoromethyl, alkyl or by alkoxy, it also being possible for one of the two radicals $R_1$ and $R_2$ to be hydrogen, or $R_1$ and $R_2$ together form an alkylene chain having from 2 to 5 carbon atoms that is unsubstituted or substituted by alkyl; or salts thereof.

The above-mentioned use against tumours and other proliferative diseases, such as psoriasis, was not to be expected in any form. The same applies to the mode of action via protein kinase inhibition described below.

Accordingly, the invention relates to the use of those compounds in a process or a method for the therapeutic treatment of warm-blooded animals, or to the use thereof in the preparation of pharmaceutical compositions for the treatment of the diseases mentioned hereinbefore and hereinafter and, further, to corresponding pharmaceutical compositions for use in the treatment of the diseases described hereinbefore and hereinafter.

Within the context of the present text, the general terms used hereinbefore and hereinafter have preferably the following meanings:

The prefix "lower" denotes a radical having up to and not more than 7 carbon atoms, especially having up to and not more than 4 carbon atoms, and most especially having 1 or 2 carbon atoms.

"Further" generally precedes radicals or conditions that are not as greatly preferred as those mentioned before them.

When asymmetric carbon atoms are present, the compounds of formula I may be in the form of mixtures of enantiomers or (where two or more centres of asymmetry are present) mixtures of diastereoisomers, or in the form of the pure enantiomers or diastereoisomers.

Halogen is preferably fluorine, chlorine, bromine or iodine, especially fluorine, chlorine or bromine, more especially bromine, and most especially chlorine.

Alkyl is unbranched or branched one or more times and preferably has up to a maximum of 20 carbon atoms. Preference is given to lower alkyl, especially n-propyl, isopropyl, n-butyl, isobutyl, sec-butyl, tert-butyl, n-pentyl, neopentyl, n-hexyl, more especially ethyl and most especially methyl.

Alkoxy contains an alkyl radical as last defined and is especially lower alkoxy, such as n-propoxy, isopropoxy, n-butoxy, isobutoxy, sec-butoxy, tert-butoxy, n-pentyloxy, neo-pentyloxy, n-hexyloxy, more especially ethoxy and most especially methoxy.

The phenyl ring in formula I that is unsubstituted or substituted by R, which is selected from halogen, trifluoromethyl, alkyl and alkoxy, is substituted by one or more (maximum n=5), especially by up to 2 (n=1 or 2), substituents R, which may be in the o-, m- or p-position (substituents that occupy a large amount of space, such as branched alkyl, for example tert-butoxy, preferably not being in the o-position), especially in the m-position; preference is given (especially when $R_1$ and $R_2$ are each lower alkyl, such as methyl) to the unsubstituted phenyl radical (n=0), to the phenyl radical that is di- or especially monosubstituted (n=1 or 2) in the m-position by halogen, especially fluorine and more especially chlorine or bromine, to the phenyl radical that is di- or especially mono-substituted (n=1 or 2) in the o-, m- or p-position (especially in the m-position) by lower alkoxy, especially ethoxy and more especially methoxy, and/or to the phenyl radical that is di- or especially mono-substituted (n=1 or 2) in the m-position by lower alkyl, especially methyl; and/or (when $R_1$ and $R_2$ together are alkylene having from 2 to 5 carbon atoms, especially tetramethylene) to the phenyl radical that is unsubstituted or di- or especially mono-substituted (n=1 or 2) by halogen, especially fluorine or more especially bromine or chlorine, by trifluoromethyl, by lower alkoxy, such as ethoxy or especially methoxy, and/or in the m-position by lower alkyl, especially methyl. Special preference is given to unsubstituted phenyl (n=0), m-chlorophenyl, m-bromophenyl or, further, m-fluorophenyl, m,m-dichlorophenyl, m,m-dibromophenyl, m-methoxyphenyl or m-trifluoromethylphenyl; or, further, m-methylphenyl or m,p-dichlorophenyl (n=0, 1 or 2).

The radicals $R_1$ and $R_2$ defined independently of one another may be different from one another or, preferably, identical.

Alkyl $R_1$ and $R_2$ preferably has the meanings mentioned above for alkyl, especially the meanings mentioned as being preferred, and is especially ethyl or more especially methyl.

Phenyl that is unsubstituted or substituted by halogen, trifluoromethyl, alkyl or by alkoxy is especially phenyl that is o-, m- or p-substituted by one or more, especially 1 or 2, radicals selected from halogen, especially fluorine, chlorine or bromine, trifluoromethyl, lower alkyl, especially methyl or, further, ethyl, and lower alkoxy, such as methoxy or, further, ethoxy (bulky substituents, such as tert-butoxy, in the o-position preferably being excepted where they cannot be prepared) or unsubstituted phenyl, and is especially phenyl; or 2-, 3- or especially 4-lower alkoxyphenyl or di-lower alkoxyphenyl, such as 2,5-di-lower alkoxyphenyl, wherein lower alkoxy is preferably methoxy.

An alkylene chain having from 2 to 5 carbon atoms formed from $R_1$ and $R_2$ together is an ethylene chain, a propylene chain or preferably a pentylene chain or especially a butylene chain, each of which is substituted by alkyl, as defined above, especially by methyl or ethyl, or preferably is unsubstituted.

The following combinations of $R_1$ and $R_2$ are preferred: $R_1$ is lower alkyl and $R_2$ is lower alkyl, especially methyl in each case; or $R_1$ and $R_2$ together are pentamethylene or especially tetramethylene; or $R_1$ is hydrogen and $R_2$ is phenyl, 2-, 3- or 4-lower alkoxyphenyl or di-lower alkoxyphenyl, such as 2,5-di-lower alkoxyphenyl, wherein lower alkoxy is in each case preferably methoxy.

Since the compounds of formula I have basic properties, salts thereof are acid addition salts with organic or inorganic acids, especially the pharmaceutically acceptable, non-toxic salts. Suitable inorganic acids are, for example, carbonic acid (preferably in the form of the carbonates or hydrogen carbonates); hydrohalic acids, such as hydrochloric acid; sulfuric acid; or phosphoric acid. Suitable organic acids are, for example, carboxylic, phosphonic, sulfonic or sulfamic acids, e.g. acetic acid, propionic acid, octanoic acid, decanoic acid, dodecanoic acid, glycolic acid, lactic acid, 2-hydroxybutyric acid, gluconic acid, glucose-monocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylamino-acetic acid, N-acetylasparagine or N-acetylcystine, pyruvic acid, acetoacetic acid, phosphoserine, 2- or 3-glycerophosphoric acid, glucose-6-phosphoric acid, glucose-1-phosphoric acid, fructose-1,6-bisphosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, nicotinic acid, isonicotinic acid, glucuronic acid, galacturonic acid, methane- or ethane-sulfonic acid, 2-hydroxyethane-sulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methyl-sulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification it is also possible to use pharmaceutically unacceptable salts, for example picrates or perchlorates. Only the salts that are pharmaceutically acceptable and non-toxic (at the relevant doses) are used therapeutically, and those salts are therefore preferred.

The compounds of formula I, especially the novel compounds according to the invention which are mentioned hereinafter, have valuable properties which can be used pharmacologically. In particular, they exhibit specific inhibitory actions which are of pharmacological value. First and foremost, they act as tyrosine protein kinase inhibitors and/or (further) as inhibitors of serine/threonine protein kinases; for example, they exhibit a powerful inhibition of the tyrosine kinase activity of the receptor for the epidermal growth factor (EGF) and c-erbB2 kinase. Those receptor-specific enzyme activities play a key role in signal transmission in a large number of mammalian cells, including human cells, especially epithelial cells, cells of the immune system and cells of the central and peripheral nervous system. For example, the EGF-induced activation of the receptor-associated tyrosine protein kinase (EGF-R-PTK) in various types of cells is a prerequisite for cell division and hence for the proliferation of the cell population. Accordingly, by increasing the level of EGF-receptor-specific tyrosine kinase inhibitors, the multiplication of the cells is inhibited. The same applies to the other protein kinases mentioned herein-before and hereinafter.

The inhibition of the EGF-receptor-specific tyrosine protein kinase (EGF-R-PTK) can be demonstrated by means of known methods, for example using recombinant intracellular domains of the EGF-receptor (EGF-R ICD; see e.g. E. McGlynn et al., Europ. J. Biochem. 207,265–275 (1992)). As compared with the control without inhibitor, the compounds of formula I inhibit the enzyme activity by 50% (IC50) at a concentration of from 0.001 to 10 µM, preferably from 0.001 to 1 µM.

In the micromolar range too, the compounds of formula I also exhibit, for example, inhibition of the cell growth of EGF-dependent cell lines, for example the epidermoidal BALB/c mouse keratinocyte cell line (see Weissmann, B. A., and Aaronson, S. A., Cell 32, 599 (1983)) or the A431 cell line, which are recognised as being useful standard sources of EGF-dependent epithelial cells (see Carpenter, G., and Zendegni, J. Anal. Biochem. 153, 279–282 (1985)). In a known test method (see Meyer et al., Int. J. Cancer 43, 851 (1989)), the inhibitory action of the compounds of formula I is, briefly, determined as follows: BALB/MK cells (10 000/microtitre plate well) are transferred to 96-well microtitre plates. The test compounds (dissolved in DMSO) are added in a series of concentrations (dilution series), so that the final concentration of DMSO is not greater than 1% (v/v). After the addition, the plates are incubated for three days, during which time the control cultures without test compound are able to undergo at least three cell division cycles. The growth of the MK cells is measured by means of methylene blue staining: after incubation, the cells are fixed with glutaraldehyde, washed with water and stained with 0.05% methylene blue. After a washing step, the dye is eluted with 3% HCl and the optical density per well in the microtitre plate is measured using a Titertek Multiskan at 665 nm. $IC_{50}$ values are calculated by means of a computer-assisted system using the formula:

$$IC_{50}=(OD_{test}-OD_{start})/(OD_{control}-OD_{start})\times 100.$$

In these experiments, the $IC_{50}$ value is the concentration of the test compound in question that results in a cell number that is reduced by 50% as compared with the control without inhibitor. The compounds of formula I exhibit inhibitory actions in the micromolar range, for example an $IC_{50}$ of approximately from 0.2 to 20 µM, especially from 0.2 to 10 µM.

The compounds of formula I also exhibit inhibition of the growth of tumour cells in vivo, as is demonstrated, for example, by the test described below: The test is based on the inhibition of the growth of the human epidermoid carcinoma A431 (ATCC No. CRL 1555; American Type Culture Collection, Rockville, Md., USA; see Santon, J. B., et al., Cancer Research 46, 4701–4705 (1986) and Ozawa, S., et al., Int. J. Cancer 40, 706–710 (1987)), which is transplanted into naked female BALB/c mice (Bomholtgard, Denmark). The growth of that carcinoma correlates with the extent of EGF-receptor expression. In the experiment, tumours having a volume of approximately 1 cm$^3$ which have been cultured in vivo are removed from test animals under sterile conditions. The tumours are comminuted and suspended in 10 volumes (w/v) of phosphate-buffered saline.

The suspension is injected s.c. (0.2 ml/mouse in phosphate-buffered saline) into the left flank of the animals. Alternatively, 1×10$^6$ cells from an in vitro culture in 0.2 ml of phosphate-buffered saline may be injected. Treatment with test compounds of formula I is begun 5 or 7 days after transplantation, when the tumours have reached a diameter of from 4 to 5 mm. The test compound in question is administered (at different doses for different groups of animals) once daily p.o. or i.p. for a period of 15 successive days (for example, dissolved in dimethyl sulfoxide/®Tween 80 [polyoxyethylene(20) sorbitan monooleate; trade mark of ICI Americas, Inc, USA]/0.9% NaCl in H$_2$O). The growth of the tumours is determined by measuring the diameter of the tumours along three axes that are perpendicular to one another. The volumes of the tumours are calculated using the known formula $\pi \times L \times D^2 / 6$ (see Evans, B. D., et al., Brit. J. Cancer 45, 466–468 (1982)). The results are given as treatment/control percentage values (T/C×100= T/C %). Pronounced inhibition of tumour growth is found, for example T/C % values of less than 50, which represents a pronounced inhibition of tumour growth.

In addition to or instead of inhibiting EGF-receptor tyrosine protein kinase, the compounds of formula I also inhibit other tyrosine protein kinases that are involved in signal transmission mediated by trophic factors, for example abl kinase, kinases from the family of the src kinases and c-erbB2 kinase (HER-2), as well as serine/threonine kinases, for example protein kinase C or CDC kinases, all of which play a pan in growth regulation and transformation in mammalian cells, including human cells.

The inhibition of c-erbB2-tyrosine kinase (HER-2) can be determined, for example, analogously to the method used for EGF-R-PTK (see C. House et al., Europ. J. Biochem. 140, 363–367 (1984)). c-erbB2 kinase can be isolated and its activity determined according to protocols known per se (see T. Akiyama et al., Science 232, 1644 (1986)).

Accordingly, the compounds of formula I that inhibit the tyrosine kinase activity of the receptor for the epidermal growth factor (EGF) and, further, of the other tyrosine protein kinases mentioned can be used, for example, in the treatment of benign or malignant tumours. They are able to bring about the regression of tumours and prevent tumour metastasisation and the growth of micrometastases. In particular, they can be used in the case of epidermal hyper-proliferation (psoriasis), in the treatment of neoplasias of epithelial nature, for example mammary carcinomas, and/or in the case of leukaemias (especially chronic myeloid leukaemia=CML). Further, the compounds of formula I (especially the novel compounds) can be used in the treatment of diseases of the immune system, insofar as several or, especially, single tyrosine protein kinases and/or (further) serine/threonine protein kinases are involved; those compounds of formula I may also be used in the treatment of diseases of the central or peripheral nervous system, insofar as signal transmission by several or, preferably, one tyrosine protein kinase(s) and/or (further) serine/threonine protein kinase(s) is involved.

The compounds of formula I are suitable for the treatment not only of humans but also of other mammals, for example of commercially usable animals, such as rodents, for example mice, rabbits or rats. They can also be used as standards in the above-mentioned tests in order to permit comparison with other compounds.

In general, the present invention relates also to the use of the compounds of formula I in the inhibition of the mentioned protein kinases.

The compounds of formula I may also be used for diagnostic purposes; for example, proliferating cells, such as tumour cells, obtained from mammals, such as humans, which will also grow in cell culture may be tested in cell culture for their sensitivity to compounds of formula I, thus allowing better determination of possible methods of treatment.

The compounds according to the invention may be used either on their own or in combination with other pharmacologically active substances, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antioestrogens and/or cytostatics.

In the case of the preferred subjects of the invention mentioned hereinafter, instead of general definitions there may be used the more specific definitions mentioned at the beginning, where appropriate and expedient.

There are preferably used compounds of formula I wherein n is from 0 to 2 and R is a substituent selected from halogen, especially fluorine or more especially chlorine or bromine, lower alkoxy, such as methoxy, and, further, from trifluoromethyl and lower alkyl, such as methyl or ethyl, the mentioned substituents preferably being in the m-position of the phenyl ring; and $R_1$ and $R_2$ are as defined above and are especially each independently of the other lower alkyl, especially ethyl or more especially methyl, or phenyl that is unsubstituted or substituted by halogen, especially fluorine, chlorine or bromine; by trifluoromethyl; by lower alkyl, such as methyl or ethyl; or by lower alkoxy, such as methoxy or ethoxy, it also being possible for one of the radicals $R_1$ and $R_2$ to be hydrogen, or $R_1$ and $R_2$ together form an alkylene chain having 4 or 5 carbon atoms that is unsubstituted or substituted by lower alkyl, such as methyl or ethyl; or salts thereof.

The invention relates also to novel compounds of formula I and to the use thereof in the processes and pharmaceutical compositions mentioned hereinbefore and hereinafter, and to pharmaceutical compositions comprising those compounds, those compounds being especially the compounds mentioned below:

Those compounds of formula I include especially those wherein n is from 0 to 5, especially 0, 1 or 2, and R is a substituent selected from halogen, alkyl, trifluoromethyl and alkoxy; $R_1$ and $R_2$ are each independently of the other alkyl, or phenyl that is unsubstituted or substituted by halogen, trifluoromethyl, alkyl or by alkoxy, it also being possible (preferably) for one of the radicals $R_1$ and $R_2$ to be hydrogen; wherein, when neither of the two radicals $R_1$ and $R_2$ is hydrogen and n is 1 or 2, preferably 1, R is bonded in the m-position (n=1) or in the m,m-position (n=2) and is selected from fluorine and especially chlorine and bromine; and (further) from lower alkoxy, especially methoxy, and, further, lower alkyl, especially methyl, and (less preferably) trifluoromethyl, and the other radicals are as last defined; or salts thereof.

Preference is given to compounds of formula I wherein n is 1 or 2, preferably 1, R is bonded in the m-position (n=1) or in the m,m-position (n=2) and is selected from fluorine and especially chlorine or bromine; and (further) from lower alkoxy, especially methoxy, and, further, lower alkyl, especially methyl, and (less preferably) trifluoro-methyl, and the other radicals are as defined in the definition of the substituents in formula I; especially, $R_1$ and $R_2$ are each independently of the other lower alkyl, especially ethyl or more especially methyl, or phenyl that is unsubstituted or substituted by fluorine, chlorine or bromine, trifluoromethyl, lower alkyl, such as methyl or ethyl, or by one or two lower alkoxy radicals, such as methoxy or ethoxy, it also being possible for one of the two radicals $R_1$ and $R_2$ to be hydrogen, or $R_1$ and $R_2$ together form an alkylene chain having 4 or 5 carbon atoms that is unsubstituted or substituted by lower alkyl, such as methyl or ethyl; or salts thereof.

Preference is given also to compounds of formula I wherein n is from 0 to 5, especially 0, 1 or 2, and R is a substituent selected from halogen, alkyl, trifluoromethyl and alkoxy; and one of the radicals $R_1$ and $R_2$ is hydrogen and the other is alkyl, or phenyl that is unsubstituted or substituted by halogen, trifluoromethyl, alkyl or by alkoxy; or salts thereof.

Greater preference is given to compounds of formula I wherein n is 1; R is chlorine or bromine bonded in the m-position; and either a) $R_1$ and $R_2$ are each lower alkyl, especially methyl; or
b) $R_1$ and $R_2$ together are pentamethylene or especially tetramethylene (-$(CH_2)_4$-); or
c) $R_1$ is lower alkyl, for example methyl, or especially is hydrogen, and $R_2$ is phenyl; or 2-, 3- or especially 4-lower alkoxyphenyl or di-lower alkoxyphenyl, especially 2,5-di-lower alkoxyphenyl, with lower alkoxy in each case preferably being methoxy; or salts thereof.

Special preference is given to compounds of formula I wherein n is 1, R is bonded in the m-position and is bromine or especially chlorine or, further, fluorine or methyl; and $R_1$ and $R_2$ are each independently of the other lower alkyl, especially methyl, or, further, phenyl, or $R_1$ and $R_2$ together form a tetramethylene radical, or salts thereof.

Very special preference is given to compounds of formula I wherein n is 1, R is fluorine or methyl or especially chlorine or bromine bonded in the m-position, and $R_1$ and $R_2$ are each methyl, or salts thereof.

Very special preference is given also to compounds of formula I wherein n is 1 or 2 and R is fluorine or methyl or especially chlorine or bromine bonded in the m-position (n=1) or in the m- and p-positions (n=2), and wherein $R_1$ and $R_2$ together form an alkylene chain having 4 or, further, 5 carbon atoms, or salts thereof.

Very special preference is given also to compounds of formula I wherein n is 1; R is chlorine or bromine bonded in the m-position; $R_1$ is hydrogen; and $R_2$ is 2-, 3- or especially 4-lower alkoxyphenyl or di-lower alkoxyphenyl, especially 2,5-di-lower alkoxy-phenyl, wherein lower alkoxy is preferably in each case methoxy; or a salt thereof.

The following individual compounds or their salts are very especially preferred:

1) 4-(m-chloroanilino)-5,6-dimethyl-7H-pyrrolo[2,3-d] pyrimidine,
2) 4-(m-bromoanilino)-5,6-dimethyl-7H-pyrrolo[2,3-d] pyrimidine,
3) 4-(m-fluoroanilino)-5,6-dimethyl-7H-pyrrolo[2,3-d] pyrimidine,
4) 4-(m,m-dichloroanilino)-5,6-dimethyl-7H-pyrrolo[2,3-d]pyrimidine,
5) 4-(m-methylanilino)-5,6-dimethyl-7H-pyrrolo[2,3-d] pyrimidine,
6) 4-(m-methoxyanilino)-5,6-dimethyl-7H-pyrrolo[2,3-d] pyrimidine,
7) 4-(m-chloroanilino)-5,6-tetramethylene-7H-pyrrolo[2,3-d]pyrimidine,
8) 4-(m-bromoanilino)-5,6-tetramethylene-7H-pyrrolo[2,3-d]pyrimidine,
9) 4-(m-fluoroanilino)-5,6-tetramethylene-7H-pyrrolo[2,3-d]pyrimidine,
10) 4-(m-methylanilino)-5,6-tetramethylene-7H-pyrrolo[2,3-d]pyrimidine,
11) 4-(m-methoxyanilino)-5,6-tetramethylene-7H-pyrrolo[2,3-d]pyrimidine,
12) 4-(m-chloroanilino)-5,6-diphenyl-7H-pyrrolo[2,3-d] pyrimidine,
13) 4-(m-bromoanilino)-5,6-diphenyl-7H-pyrrolo[2,3-d] pyrimidine,
14) 4-(m-trifluoromethylanilino)-5,6-tetramethylene-7H-pyrrolo[2,3-d]pyrimidine,
15) 4-(m,p-dichloromethylanilino)-5,6-tetramethylene-7H-pyrrolo[2,3-d]pyrimidine,
16) 4-(m-chloroanilino)-6-(4-methoxyphenyl)-7H-pyrrolo[2,3-d]pyrimidine,
17) 4-(m-chloroanilino)-6-(2,5-dimethoxyphenyl)-7H-pyrrolo[2,3-d]pyrimidine,
18) 4-(m-chloroanilino)-6-(phenyl)-7H-pyrrolo[2,3-d] pyrimidine,
19) 4-(m-chloroanilino)-5-methyl-6-(4-methoxyphenyl)-7H-pyrrolo[2,3-d]pyrimidine,
20) 4-(m-chloroanilino)-6-(3-methoxyphenyl)-7H-pyrrolo[2,3-d]pyrimidine, and/or
21) 4-(m-chloroanilino)-6-(2-methoxyphenyl)-7H-pyrrolo[2,3-d]pyrimidine.

Of those compounds and salts, those having the numbers 1), 2), 7) and 8) as well as 16), 17), 18), 20), 21) and, further, 19) are most especially preferred.

Very great preference is given to the use of the above-mentioned novel compounds and more especially of the compounds mentioned in the Examples as active ingredients in the above-mentioned uses, processes and pharmaceutical compositions. The novel compounds and salts mentioned specifically in the Examples are very especially preferred.

The compounds of formula I can be prepared in a manner known Der se (see German Offenlegungsschrift DE-OS 30 36 390, published on 13th May 1982, and Jorgensen, A., et al., J. Heterocycl. Chem. 22, 859 (1985)), for example by a) reacting a halo-pyrrolo-pyrimidine of formula II

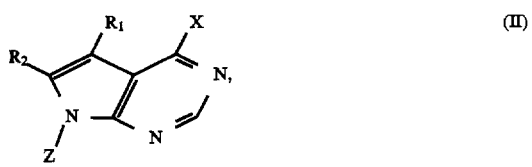

wherein $R_1$ and $R_2$ are as defined for compounds of formula I, Z is hydrogen or 1-aryl-lower alkan-1-yl and X is a halogen atom, with a phenylamine of formula III

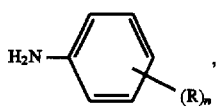
(III)

wherein R and n are as defined for compounds of formula I, and, when Z is 1-aryl-lower alkan-1-yl, removing the radical with dealkylation; or b) reacting a pyrrolo-pyrimidinone of formula IV

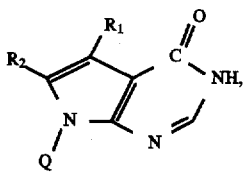
(IV)

wherein $R_1$ and $R_2$ are as defined for compounds of formula I and Q is hydrogen or 1-aryl-lower alkan-1-yl, with a phenylamine of formula III as mentioned above, in the presence of a dehydrating agent and a tertiary amine, and, if desired, converting a resulting free compound of formula I into a salt, converting a resulting salt of a compound of formula I into the free compound or into a different salt, and/or separating a mixture of isomeric compounds of formula I into the individual isomers.

More detailed description of the process

In the following more detailed description of the preparation process, the radicals R, $R_1$ and $R_2$ and n are as defined for compounds of formula I, unless indicated otherwise.

Process a)

In the compound of formula II, the halogen X is bromine, iodine or, especially, chlorine. 1-Aryl-lower alkan-1-yl Z is preferably 1-phenyl-lower alkyl, especially 1-phenylethyl or, more especially, benzyl.

The reaction between the halide of formula II and the amine of formula III is carried out in suitable inert polar solvents, especially alcohols, for example lower alkanols, such as methanol, propanol or, especially, ethanol or n-butanol. The reaction is carried out at elevated temperatures, preferably under reflux conditions.

When Z in the compound of formula II is 1-aryl-lower alkan-1-yl (i.e. when a compound of formula VIII containing a corresponding radical Q, as defined below, is present as starting material), that radical is removed in the resulting precursor of the compound of formula I (with Z instead of the hydrogen atom at the nitrogen).

That is effected by removing the 1-aryl-lower alkan-1-yl radical Q with dealkylation, for example by treatment with protonic acids, such as hydrochloric acid, phosphoric acids or polyphosphoric acid, at preferred temperatures of from 20° to 150° C.and in the absence or presence of water (that is especially the preferred method where Z=1-phenylethyl); or, preferably, by treatment with Lewis acids, especially $AlCl_3$, in aromatic solvents, especially benzene and/or toluene, at elevated temperature, especially under reflux (that is especially the preferred variant where Z=benzyl; see also the analogous process in Chem. Pharm. Bull. 39(5), 1152 (1991)).

Process b) 1-Aryl-lower alkan-1-yl Q in a compound of formula IV is especially 1-phenylethyl and, further, benzyl.

The compound of formula IV is in tautomeric equilibrium (lactam/lactim form), the lactam form (formula IV) presumably being predominant. Formula IV is used to represent the two possible tautomeric forms.

The lactim form has the formula IVA

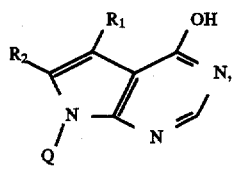
(IVA)

wherein the radicals are as defined for compounds of formula IV. In a compound of formula IV or IVA, the radical Q is preferably 1-aryl-lower alkan-1-yl.

The reaction between the pyrrolo-pyrimidinone of formula IV and the phenylamine of formula III is carried out at elevated temperature, for example at from 200° to 250° C. There is used as the dehydrating agent especially a strong chemical dehydrating agent, especially phosphorus pentoxide ($P_4O_{10}$).

There is suitable as the tertiary amine especially ammonia substituted by three radicals selected independently of one another from alkyl, especially lower alkyl, such as methyl or ethyl, and cycloalkyl having from 3 to 7 carbon atoms, especially cyclohexyl, for example N,N-dimethyl-N-cyclohexylamine, N-ethyl-N,N-diisopropylamine or triethyl-amine, or, further, pyridine, N-methylmorpholine or 4-dimethylaminopyridine.

Starting Materials:

The starting materials of formulae II and IV can be obtained in accordance with the following reaction scheme (reaction steps (A) to (D)):

Reaction scheme for the preparation of compounds of formulae II and IV

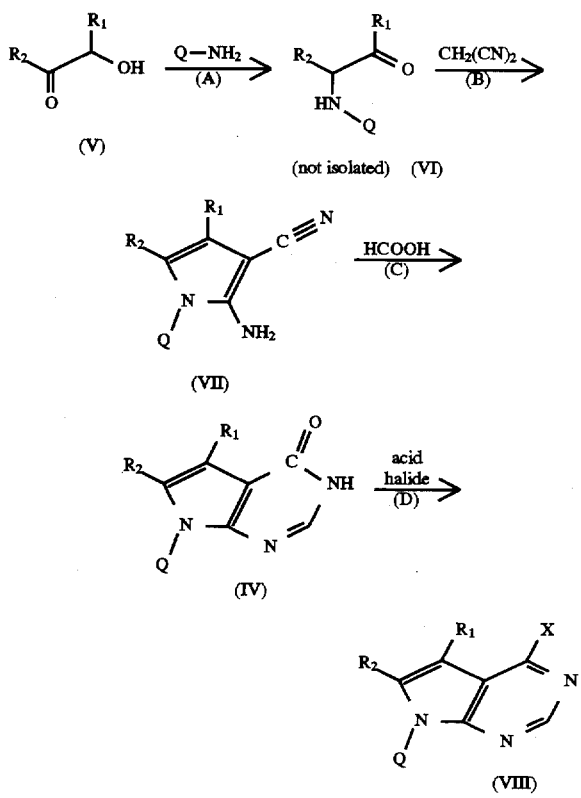

The compound of formula VIII is already a compound of formula II wherein instead of Z there is present the radical Q, which is hydrogen or 1-aryl-lower alkan-1-yl (especially 1-phenyl-lower alkyl, such as benzyl or 1-phenylethyl); in the compounds of formulae IV, V, VI, VII and VIII, the radicals $R_1$ and $R_2$ are as defined for compounds of formula I, while Q (also in the nitrogen compounds of the formula Q—$NH_2$) is hydrogen or 1-aryl-lower alkan-1-yl (especially 1-phenyl-lower alkyl, such as benzyl or 1-phenylethyl). In the compound of formula VIII, X is a halogen atom selected from bromine, iodine and, especially, chlorine.

The 1-(Q)-2-amino-3-cyano-pyrroles of formula VII used as intermediates can be prepared in good yields in process steps (A) and (B) according to published processes known per se (see, for example, Roth, H. J., and Eger, K., Arch. Pharmaz. 308, 179 (1975)). The benzyl-protected 4-(X)-pyrrolo-pyrimidines of formula VIII (Q=benzyl; X=bromine, iodine or, especially, chlorine) are novel, and the present invention relates also thereto; they can be prepared according to processes analogous to those described in German Offenlegungsschrift DE-OS 28 18 676 (published 8th Nov. 1979) and DE-OS 30 36 390 (published 13th May 1982).

In detail, reaction (A) with the nitrogen compound Q—$NH_2$ is carried out under customary condensation conditions, for example in the presence of catalytic amounts of a strong acid, for example hydrochloric acid or p-toluenesulfonic acid, at elevated temperature (preferably boiling heat) in a suitable solvent, for example benzene or toluene, with the separation of water, to form the respective α-amino ketone of formula VI. That compound is not isolated but is immediately condensed with malonic acid dinitrile in process step (B), while hot and with further separation of water, if necessary with the addition of a small amount of a base, such as piperidine, to yield a compound of formula VII.

The compound of formula VII is then reacted in process step (C) with formic acid (which is preferably used in excess relative to the compound of formula VII, for example in a 10- to 30- fold molar excess), in the absence or presence of inert solvents, such as dimethyl-formamide, at elevated temperature, for example at temperatures of from 80° C. to the boiling temperature, to yield a 4-hydroxy-pyrrolo-pyrimidine of formula IV.

The compound of formula IV may then either be used directly in process b) (see above), or be reacted with an acid halide (process step (D)) to yield a compound of formula VIII (wherein halogen is bromine, iodine or, especially, chlorine, i.e. is the radical X as is to be introduced into the compound of formula VIII). Suitable acid halides are, for example, organic acid halides, such as lower alkanoyl bromides, iodides or, especially, chlorides, or especially sulfonic acid bromides, iodides or, especially, chlorides, such as p-toluene-sulfonic acid chloride, or especially inorganic acid bromides, iodides or, especially, chlorides, such as $POCl_3$ (which is especially preferred), $PCl_5$ or $SOCl_2$ (for X=Cl) or, further, $PBr_5$, $SOBr_2$ (for X=Br) or $PI_5$ (X=I). The reaction is carried out at elevated temperature, for example at reflux temperature, if necessary in the presence of an inert solvent.

From the compound of formula VIII wherein Q is a 1-aryl-lower alkan-1-yl radical it is possible to prepare a compound of formula II wherein Z is hydrogen by removing the 1-aryl-lower alkan-1-yl radical Q with dealkylation, for example by treatment with protonic acids, such as hydrochloric acid, phosphoric acids or polyphosphoric acid, at preferred temperatures of from 20° to 150° C. and in the absence or presence of water (that is especially the preferred method where Q=1-phenylethyl); or preferably by treatment with Lewis acids, especially $AlCl_3$, in an aromatic solvent, especially in benzene and/or toluene, at elevated temperature, especially under reflux (that is especially the preferred variant where Q=benzyl; see also the analogous process in Chem. Pharm. Bull. 39(5), 1152 (1991)).

A compound of formula IV wherein $R_1$ is hydrogen or lower alkyl, $R_2$ is phenyl that is unsubstituted or substituted by halogen, trifluoromethyl, alkyl or by alkoxy, and Q is hydrogen can also be obtained in accordance with the following reaction scheme {reaction steps (E) and (F)}:

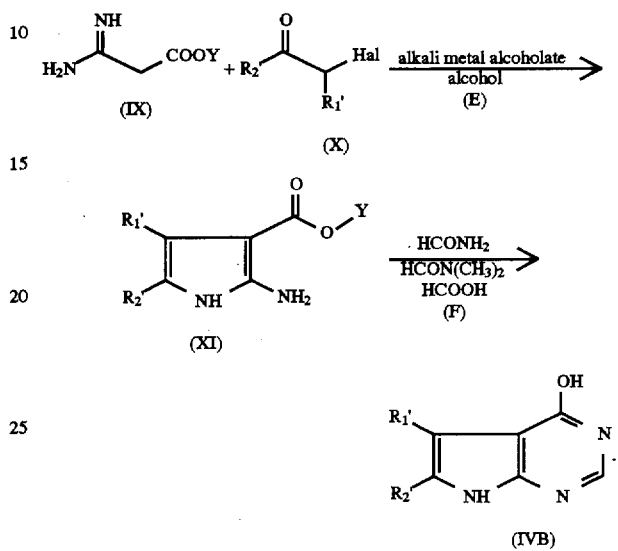

The compound of formula IVB falls within the definition of compounds of formula IV (with analogous lactim/lactam tautomerism, formula IVB being representative of both tautomeric forms) and corresponds to a compound of formula IV that is to be prepared wherein $R_1$ is hydrogen or lower alkyl, $R_2$ is phenyl that is unsubstituted or substituted by halogen, trifluoromethyl, alkyl or by alkoxy, and Q is hydrogen. In the compounds of formulae X, XI and IVB, $R_1'$ is hydrogen or lower alkyl (corresponding to the radical $R_1$ in the compound of formula IV that is to be prepared) and $R_2'$ is phenyl that is unsubstituted or substituted by halogen, trifluoromethyl, alkyl or by alkoxy (corresponding to the radical $R_2$ in the compound of formula IV that is to be prepared). Y in compounds of formulae IX and XI is an alkyl radical, such as lower alkyl, especially ethyl. Hal in formula X is a chlorine atom, an iodine atom or, especially, a bromine atom (a different leaving group, such as toluenesulfonyloxy or a comparable sulfonyl radical, would also be possible).

In detail, the reaction (E) is carried out in the presence of an alkali metal alcoholate, such as a potassium or, especially, sodium alcoholate, there being present as the alcoholate radical preferably the radical of an alkanol, such as a lower alkanol, such as methanol or ethanol, especially in the presence of sodium ethanolate or, further, sodium methanolate, in the presence of the corresponding alcohol, at preferred temperatures of from −15° to 50° C., especially from approximately 0° C. to room temperature, preferably under a protecting gas, such as argon.

The corresponding compound of formula XI is obtained and (preferably after purification) is reacted in process step (F) with formamide ($HCONH_2$) [preferably in the presence of suitable solvents, such as N,N-dimethylformamide ($HCON(CH_3)_2$) or other N,N-di-lower alkylamides and in the presence of formic acid, at preferred temperatures of from 100° to 200° C., especially from 140° to 160° C., to yield the compound of formula IVB.

In the diagram showing process steps (A) to (D) and (E) to (F), secondary products that are not important to the reaction have for the sake of simplicity not been included in the formulae shown above.

Amidinoacetic acid esters of formula IX are known or can be prepared according to processes known per se.

α-Haloketones of formula X are known, can be prepared according to processes known per se or are available commercially.

The phenylamines of formula III are known, are available commercially and/or can be prepared according to processes known per se.

General Process Conditions:

Free compounds of formula I having salt-forming properties that are obtainable in accordance with the process can be converted into their salts in a manner known per se, for example by treatment with acids or suitable derivatives thereof, for example by the addition of the acid in question to the compound of formula I dissolved in a suitable solvent, for example an ether, such as a cyclic ether, especially dioxane or more especially tetrahydrofuran.

Mixtures of isomers obtainable according to the invention can be separated into the individual isomers in a manner known per se; racemates can be separated, for example, by the formation of salts with optically pure salt-forming reagents and separation of the diastereoisomeric mixture so obtainable, for example by means of fractional crystallisation.

The reactions mentioned above can be carded out under reaction conditions that are known per se, in the absence or, customarily, in the presence of solvents or diluents, preferably solvents or diluents that are inert towards the reagents used and are solvents therefor, in the absence or presence of catalysts, condensation agents (e.g. phosphorus pentoxide) or neutralising agents, for example bases, especially nitrogen bases, such as tri-ethylamine hydrochloride, depending on the nature of the reaction and/or of the reactants at reduced, normal or elevated temperature, for example in a temperature range of from approximately −80° C. to approximately 200° C., preferably from approximately −20° C. to approximately 150° C., for example at the boiling point of the solvent used, under atmospheric pressure or in a closed vessel, where appropriate under pressure, and/or in an inert atmosphere, for example under a nitrogen atmosphere.

Preference is given to the reaction conditions mentioned specifically in each case.

Solvents and diluents are, for example, water, alcohols, for example lower alkyl hydroxides, such as methanol, ethanol, propanol or, especially, butanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), carboxylic acids, especially formic acid or acetic acid, amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, acid anhydrides, such as acetic anhydride, esters, such as ethyl acetate, bisalkanesulfines, such as dimethyl sulfoxide, nitrogen heterocycles, such as pyridine, hydrocarbons, for example lower alkanes, such as heptane, or aromatic compounds, such as benzene, toluene or xylene(s), or mixtures of those solvents, it being possible to select the solvents that are suitable for each of the above-mentioned reactions.

For working up the obtainable compounds of formula I or their salts there are used customary processes, for example solvolysis of excess reagents; recrystallisation; chromatography, for example partition, ion or gel chromatography; partitioning between inorganic and organic solvent phases; extraction one or more times, especially after acidification or increasing the basicity or the salt content; drying over hygroscopic salts; digestion; filtration; washing; dissolution; concentration by evaporation (if necessary in vacuo or under a high vacuum); distillation; crystallisation, for example of resulting compounds in oil form or from the mother liquor, inoculation with a crystal of the end product also being possible; or a combination of two or more of the mentioned working-up steps, which may also be used repeatedly.

Starting materials and intermediates may be used in pure form, for example after working up as mentioned above, in partially purified form or, for example, directly in the form of a crude product.

In view of the close relationship between the compounds of formula I in free form and in the form of salts, any reference hereinbefore and hereinafter to the free compounds or their salts is be understood as meaning also the corresponding salts or free compounds, respectively, where appropriate and expedient, provided that the compounds contain salt-forming groups.

The compounds, including their salts, may also be obtained in the form of hydrates, or their crystals may include, for example, the solvent used for crystallisation.

In the process of the present invention there are preferably used those starting materials which result in the novel compounds of formula I described at the beginning as being especially valuable.

The invention relates also to those forms of the process in which a compound obtainable as an intermediate at any stage of the process is used as starting material and the remaining process steps are carded out, or in which a starting material is formed under the reaction conditions or is used in the form of a derivative, for example a salt thereof.

Pharmaceutical Compositions the Preparation thereof, and the use According to the Invention of the Compounds of Formula I and Compositions Comprising those Compounds as Active Ingredient The present invention relates also to pharmaceutical compositions that comprise one of the compounds of formula I as active ingredient and that can be used especially in the treatment of the diseases mentioned at the beginning. Special preference is given to compositions for enteral, such as nasal, buccal, rectal or, especially, oral, and parenteral, such as intravenous, intramuscular or subcutaneous, administration to warm-blooded animals, especially humans. The compositions comprise the active ingredient on its own or, preferably, together with a pharmaceutically acceptable carder. The dose of active ingredient depends on the disease to be treated, and on the species, its age, weight and individual condition, on individual pharmacokinetic conditions, and on the mode of administration.

The invention relates also to pharmaceutical compositions for use in a method for the prophylactic or, especially, therapeutic treatment of the human or animal body, to a process for the preparation thereof (especially as compositions for the treatment of tumours), and to a method of treating tumour diseases, especially those mentioned above.

The invention relates also to processes, and to the use of compounds of formula I in the preparation of pharmaceutical compositions that comprise compounds of formula I as active component (active ingredient).

Preference is given to a pharmaceutical composition that is suitable for administration to a warm-blooded animal, especially a human or a commercially usable mammal, suffering from a disease that is responsive to inhibition of a protein kinase, for example psoriasis or a tumour, which composition comprises a compound of formula I, or a salt thereof where salt-forming groups are present, in an amount that is effective in inhibiting the protein kinase, together with at least one pharmaceutically acceptable carrier.

Preference is given also to a pharmaceutical composition for the prophylactic or, especially, therapeutic treatment of tumour diseases and other proliferative diseases in a warm-blooded animal, especially a human or a commercially usable mammal, which requires such treatment, especially which is suffering from such a disease, which composition comprises as active ingredient a novel compound of formula I, or a pharmaceutically acceptable salt thereof, in an amount that is prophylactically or, especially, therapeutically effective against the mentioned diseases.

The pharmaceutical compositions comprise from approximately 1% to approximately 95% active ingredient, dosage forms that are in single dose form preferably comprising from approximately 20% to approximately 90% active ingredient, and dosage forms that are not in single dose form preferably comprising from approximately 5% to approximately 20% active ingredient. Unit dose forms are, for example, dragées, tablets, ampoules, vials, suppositories or capsules. Other dosage forms are, for example, ointments, creams, pastes, foams, tinctures, lipsticks, drops, sprays, dispersions, etc. Examples are capsules comprising from approximately 0.05 g to approximately 1.0 g of the active ingredient.

The pharmaceutical compositions of the present invention are prepared in a manner known per se, for example by means of conventional mixing, granulating, confectioning, dissolving or lyophilising processes.

There are preferably used solutions of the active ingredient, additionally also suspensions or dispersions, especially isotonic aqueous solutions, dispersions or suspensions, which, for example in the case of lyophilised compositions comprising the active ingredient on its own or together with a carrier, e.g. mannitol, may be prepared before use. The pharmaceutical compositions may be sterilised and/or may comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxy-methylcellulose, carboxymethylcellulose, dextran, polyvinylpyrrolidone or gelatin, or also solubilisers, for example ®Tween 80 [polyoxyethylene(20) sorbitan monooleate; trade mark of ICI Americas, Inc, USA].

Suspensions in oil comprise as the oil component the vegetable, synthetic or semi-synthetic oils customarily used for injection purposes. There may be mentioned especially liquid fatty acid esters which contain as acid component a long-chain fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, where appropriate with the addition of anti-oxidants, for example vitamin E, β-carotene or 3,5-di-tert-butyl-4-hydroxytoluene. The alcohol component of those fatty acid esters has not more than 6 carbon atoms and is a mono- or poly-valent, for example mono-, di- or tri-valent, alcohol, for example methanol, ethanol, propanol, butanol or pentanol or their isomers, but especially glycol and glycerol. Accordingly, there may be mentioned as examples of fatty acid esters: ethyl oleate, iso-propyl myristate, isopropyl palmitate, "Labrafil M 2375" (polyoxyethylene glycerol trioleate from Gattefossé, Paris), "Labrafil M 1944 CS" (unsaturated polyglycolised glycerides prepared by alcoholysis of apricot kernel oil and composed of glycerides and polyethylene glycol esters; Gattefossé, France), "Labrasol" (saturated polyglycolised glycerides prepared by alcoholysis of TCM and composed of glycerides and polyethylene glycol esters; Gattefossé, France) and/or "Miglyol 812" (triglyceride of saturated fatty acids having a chain length of from $C_8$ to $C_{12}$ from Hüls AG, Germany), but especially vegetable oils, such as cottonseed oil, almond oil, olive oil, castor oil, sesame oil, soybean oil and, more especially, groundnut oil.

The preparation of the injection compositions is carried out in customary manner under sterile conditions, as are the introduction, for example, into ampoules or vials and the sealing of the containers.

Pharmaceutical compositions for oral administration can be obtained, for example, by combining the active ingredient with one or more solid carriers, granulating a resulting mixture, where appropriate, and processing the mixture or granules, if desired, where appropriate with the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, flee or potato starch, methylcellulose, hydroxypropylmethylcellulose, sodium carboxymethylcellulose and/or polyvinylpyrrolidone, and/or, if desired, disintegrators, such as the above-mentioned starches and also carboxymethyl starch, cross-linked polyvinylpyrrolidone, or alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, where appropriate enteric coatings, there being used inter alia concentrated sugar solutions, which may comprise gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxy-propylmethylcellulose phthalate. Colorings or pigments may be added to the tablets or dragée coatings, for example for identification purposes or to indicate different doses of active ingredient.

Pharmaceutical compositions for oral administration are also hard gelatin capsules, and soft sealed capsules consisting of gelatin and a plasticiser, such as glycerol or sorbitol. The hard gelatin capsules may comprise the active ingredient in the form of granules, for example in admixture with fillers, such as corn starch, binders and/or glidants, such as talc or magnesium stearate, and, where appropriate, stabilisers. In soft capsules the active ingredient is preferably dissolved or suspended in suitable liquid excipients, such as fatty oils, paraffin oil or liquid polyethylene glycols or fatty acid esters of ethylene glycol or propylene glycol, it likewise being possible to add stabilisers and detergents, for example of the polyoxyethylene sorbitan fatty acid ester type.

Other oral dosage forms are, for example, syrups prepared in customary manner which comprise the active ingredient, for example, in suspended form and in a concentration of approximately from 5% to 20%, preferably approximately 10% or in a similar concentration that provides a suitable single dose when administered, for example, in a measure of 5 or 10 ml. Also suitable are, for example, powdered or liquid concentrates for the preparation of shakes, for example in milk. Such concentrates may also be packed in single dose quantities.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that comprise viscosity-increasing substances, for example sodium carboxymethylcellulose, sorbitol and/or dextran, and, if desired, stabilisers. The active ingredient, where appropriate together with excipients, can also be in the form of a lyophilisate and be made into a solution prior to parenteral administration by the addition of suitable solvents.

Solutions used, for example, for parenteral administration can also be used as infusion solutions.

Preferred preservatives are, for example, antioxidants, such as ascorbic acid, or micro-bicides, such as sorbic acid or benzoic acid.

Ointments are off-in-water emulsions that comprise up to 70%, but preferably from 20 to 50%, water or aqueous phase. There are suitable as the fatty phase especially hydro-carbons, for example Vaseline®, paraffin oil or hard paraffins, which, in order to improve the water-binding capacity, preferably contain suitable hydroxy compounds, such as fatty alcohols or esters thereof, for example cetyl alcohol or wool wax alcohols, such as wool wax. Emulsifiers are corresponding lipophilic substances, such as sorbitan fatty acid esters (Spans®), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and perfumes.

Fatty ointments are anhydrous and comprise as base especially hydrocarbons, for example paraffin, Vaseline® or paraffin oil, also natural or partially synthetic fats, for example coconut fatty acid triglyceride, or preferably hardened oils, for example hydrogenated groundnut oil or castor oil, also fatty acid partial esters of glycerol, for example glycerol mono- and/or di-stearate, and also, for example, the fatty alcohols increasing water absorption, emulsifiers and/or additives mentioned in connection with the ointments.

Creams are oil-in-water emulsions that comprise more than 50% water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example Vaseline® (petrolalum) or paraffin oil. Suitable emulsifiers are surface-active substances having predominantly hydrophilic properties, such as corresponding non-ionic emulsifiers, for example fatty acid esters of polyalcohols or ethylene oxide adducts thereof, such as polyglyceric acid fatty acid esters or polyethylene sorbitan fatty acid esters (Tween®), and also polyoxyethylene fatty alcohol ethers or fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl alcohol or stearyl alcohol. Additives to the aqueous phase are inter alia agents that reduce the drying out of the creams, for example polyalcohols, such as glycerol, sorbitol, propylene glycol and/or polyethylene glycols, also preservatives and perfumes.

Pastes are creams and ointments having secretion-absorbing powder constituents, such as metal oxides, for example titanium oxide or zinc oxide, also talc and/or aluminium silicates, the purpose of which is to bind any moisture or secretions present.

Foams are administered from pressurised containers and are liquid oil-in-water emulsions in aerosol form, there being used as propellants halogenated hydrocarbons, such as chloro-fluoro-lower alkanes, for example dichlorodifluoromethane and dichlorotetrafluoroethane, or preferably non-halogenated gaseous hydrocarbons, air, $N_2O$ or carbon dioxide. As oil phase there are used inter alia the oil phases used above under ointments and creams, like-wise the additives mentioned therein.

Tinctures and solutions generally have an aqueous-ethanolic base to which there are added inter alia polyalcohols, for example glycerol, glycols and/or polyethylene glycol, as humechants for reducing evaporation, and fat-restoring substances, such as fatty acid esters with low molecular weight polyethylene glycols, that is to say lipophilic substances that are soluble in the aqueous mixture, as a replacement for the fatty substances removed from the skin by the ethanol, and, if necessary, other excipients and additives.

The invention relates also to a process or a method for the treatment of the pathological conditions mentioned above, especially those which are responsive to inhibition of protein kinases. The compounds of formula I may be administered prophylactically or therapeutically as such or in the form of pharmaceutical compositions, preferably in an amount that is effective against the mentioned diseases, to a warm-blooded animal, for example a human, requiring such treatment, the compounds being used especially in the form of pharmaceutical compositions. In the case of a body weight of approximately 70 kg, a daily dose of from approximately 0.1 g to approximately 5 g, preferably from approximately 0.5 g to approximately 2 g, of a compound of the present invention is administered.

EXAMPLES

The Examples which follow serve to illustrate the invention, without limiting the scope thereof.

Abbreviations used:

| | |
|---|---|
| TLC | thin-layer chromatogram |
| FAB-MS | Fast Atom Bombardment Mass Spectroscopy |
| sat. | saturated |
| h | hour(s) |
| hexane | n-hexane |
| min. | minute(s) |
| RT | room temperature |
| m.p. | melting point |
| THF | tetrahydrofuran |

Unless otherwise mentioned, mixtures of liquids are indicated by proportions by volume (v/v).

In $^1$H-NMR spectra, chemical shifts are given in ppm as δ value.

The precursors mentioned below relate to starting materials required for the synthesis of the Examples.

Precursor 1—1:4-Hydroxy-5,6-dimethyl-7-benzyl-pyrrolo[2,3-d]pyrimidine 9.5 g of 2-amino-4,5-dimethyl-1-benzyl-3-cyano-pyrrole (prepared from acetoin, benzyl-amine and malonodinitrile in accordance with a known process (see H. J. Roth and K. Eger, Arch. Pharmaz. 308, 179 (1975))) are boiled at 110° C. with 80 ml of 85% formic acid for 5 hours. The reaction solution is cooled in an ice-bath, whereupon light-brown crystals form. The suspension is poured onto approximately 200 ml of ice-water and stirred for approximately 10 min. The precipitate is then filtered off with suction. The crystals are washed with water and then with hexane and are dried. The title compound is obtained, m.p. 251°–253° C. (decomposition).

Precursor 2-1: 4-Hydroxy-5,6-tetramethylene-7-benzyl-pyrrolo[2,3-d]pyrimidine

In a manner analogous to that described for precursor 1—1, from 15 g of 2-amino-1-benzyl-3-cyano-4,5,6,7-tetrahydroindole and 100 ml of 85% formic acid there is obtained 4-hydroxy-5,6-tetramethylene-7-benzyl-pyrrolo[2,3-d]pyrimidine in the form of white crystals having a melting point of 104°–105° C.

$C_{17}H_{17}N_3O$: FAB-MS (M+H)+=280.

The following is prepared analogously:

Precursor 3-1: 4-Hydroxy-5,6-diphenyl-7-benzyl-pyrrolo[2,3-d]pyrimidine

Preparation from 2-amino-4,5-diphenyl-1-benzyl-3-cyano-pyrrole (prepared from benzoin, benzylamine and malonodinitrile analogously to precursor 1—1) by boiling in 85% formic acid analogously to precursor 1—1.

m.p.: 225°–230° C.

$C_{25}H_{19}N_3O$: FAB-MS (M+H)+=378.

Precursor 1-2: 4-Chloro-5,6-dimethyl-7-benzyl-pyrrolo[2,3-d]pyrimidine 2.5 g of 4-hydroxy-5,6-dimethyl-7-benzyl-pyrrolo[2,3-d]pyrimidine are boiled at reflux with 20 ml of POCl$_3$ for 2.5 hours. The brown solution is cooled to RT and poured onto ice-water. The brownish precipitate is filtered off with suction and dissolved in ethyl acetate. The ethyl acetate phase is washed with water, dried and concentrated in a rotary evaporator until white crystals form. 4-Chloro-5,6-dimethyl-7-benzyl-pyrrolo[2,3-d]-pyrimidine is obtained in the form of white crystals having a melting point of 115°–116° C.

$C_{15}H_{14}N_3Cl$: FAB-MS (M+H)+=272.

Precursor 2—2: 4-Chloro-5,6-tetramethylene-7-benzyl-pyrrolo[2,3-d]pyrimidine

In a manner analogous to that described for precursor 1-2, crude crystals of the product are obtained from 8.3 g of 4-hydroxy-5,6-tetramethylene-7-benzyl-pyrrolo[2,3-d]pyrimidine and 50 ml of POCl$_3$. After recrystallisation from ethanol, 4-chloro-5,6-tetramethylene-7-benzyl-pyrrolo[2,3-d]pyrimidine is obtained in the form of light-pink crystals having a melting point of 104°–105° C. $C_{17}H_{16}N_3Cl$: FAB-MS (M+H)+=298.

The following is prepared analogously from precursor 3–1:

Precursor 3-2: 4-Chloro-5,6-diphenyl-7-benzyl-pyrrolo[2,3-d]pyrimidine m.p.: 181°–183° C.

$C_{25}H_{18}ClN_3$: FAB-MS (M+H)+=396.

Precursor 1-3: 4-(m-Chloroanilino)-5,6-dimethyl-7-benzyl-pyrrolo[2,3-d]pyrimidine 0.6 g of 4-chloro-5,6-dimethyl-7-benzyl-pyrrolo[2,3-d] pyrimidine and 0.28 ml of m-chloroaniline are heated at reflux in 10 ml of ethanol for 17 hours. The brown solution is concentrated to dryness by evaporation, the residue is taken up in ethyl acetate, and the ethyl acetate solution is washed until neutral with sodium hydrogen carbonate solution and water, dried and concentrated by evaporation. The residue is crystallised from ethyl acetate/hexane. 4-(m-Chloroanilino)-5,6-dimethyl-7-benzyl-pyrrolo[2,3-d] pyrimidine is obtained in the form of white crystals having a melting point of 132°–133° C.

$C_{21}H_{19}N_4Cl$: FAB-MS (M+H)+=363.

The following are prepared analogously to precursor 1-3, starting from 4-chloro-5,6-dimethyl-7-benzyl-pyrrolo[2,3-d]pyrimidine:

Precursor 1-4: 4-(m-Bromoanilino)-5,6-dimethyl-7-benzyl-pyrrolo[2,3-d]pyrimidine m.p.: 131°–135° C.

$C_{21}H_{19}BrN_4$: FAB-MS (M+H)+=407.

Precursor 1-5: 4-(m-Fluoroanilino)-5,6-dimethyl-7-benzyl-pyrrolo[2,3-d]pyrimidine m.p.: 118°–120° C.

$C_{21}H_{19}FN_4$: FAB-MS (M+H)+=347.

Precursor 1-6: 4-(m,m-Dichloroanilino)-5,6-dimethyl-7-benzyl-pyrrolo[2,3-d]pyrimidine m.p.: 188°–189° C.

$C_{20}H_{18}Cl_2N_4$: FAB-MS (M+H)+=386.

Example: 1: 4-(m-Chloroanilino)-5,6-dimethyl-7H-pyrrolo[2,3-d]pyrimidine 1 g (2.76 mmol) of 4-(m-chloroanilino)-5,6-dimethyl-7-benzyl-pyrrolo[2,3-d]pyrimidine and 2.57 g (19.32 mmol) of AlCl$_3$ are heated at reflux in 20 ml of toluene for 2 hours, until all starting material has disappeared in a TLC. The reaction solution is cooled to RT, poured onto ice-water and stirred at 0° C. for 2 hours. The precipitate is filtered off with suction and dissolved in hot ethyl acetate. The ethyl acetate solution is washed twice each with 5% sodium hydrogen carbonate solution and sat. NaCl solution, is dried and is concentrated by evaporation. The residue is crystallised from ethyl acetate/hexane, yielding 4-(m-chloroanilino)-5,6-dimethyl-7H-pyrrolo[2,3-d]pyrimidine in the form of colourless crystals having a melting point of 239°–240° C.

$C_{14}H_{13}ClN_4$: FAB-MS (M+H)+=273.

For the preparation of the hydrochloride, 200 mg of 4-(m-chloroanilino)-5,6-dimethyl-7H-pyrrolo[2, 3-d] pyrimidine are dissolved in 15 ml of THF, and 0.5 ml of a 3N ethereal HCl solution is added dropwise at 0° C. After the addition of ether, white crystals of the hydrochloride form. The crystals are filtered off with suction, washed with a small amount of ether and dried.

The following compounds are prepared analogously to Example 1 from the corresponding benzyl compounds:

Example 2: 4-(m-Bromoanilino)-5,6-dimethyl-7H-pyrrolo[23-d]pyrimidine

Preparation from precursor 1-4; result: title compound m.p.: 243°–244° C.;

$C_{14}H_{13}BrN_4$: FAB-MS (M+H)+=317.

Example 3: 4-(m-Fluoroanilino-5,6-dimethyl-7H-pyrrolo[2,3-d]pyrimidine

Preparation from precursor 1-5; result: title compound m.p.: 245°–255° C.;

$C_{14}H_{13}FN_4$: FAB-MS (M+H)+=257.

Example 4: 4-(m,m-Dichloroanilino)-5,6-dimethyl-7H-pyrrolo[2,3-d]pyrimidine

Preparation from precursor 1-6; result: title compound m.p.: >250° C.;

$C_{14}H_{12}Cl_2N_4$: FAB-MS (M+H)+=307.

Precursor 1-7: 4-Chloro-5,6-dimethyl-7H-pyrrolo[2,3-d]pyrimidine m.p.: 252°–253° C.

$C_8H_8ClN_3$: FAB-MS (M+H)+=182.

Precursor 2-3: 4-Chloro-5,6-tetramethylene-7H-pyrrolo[2,3-d]pyrimidine m.p.: 244°–245° C.

$C_{10}H_{10}ClN_3$: FAB-MS (M+H)+=182.

Precursor 3—3: 4-Chloro-5,6-diphenyl-7H-pyrrolo[2,3-d]pyrimidine m.p.: 228°–230° C.

$C_{18}H_{12}ClN_3$: FAB-MS (M+H)+=306.

Analogously to the reaction for the preparation of precursor 1-3, the following compounds are prepared starting from 4-chloro-5,6-dimethyl-7H-pyrrolo[2,3-d]pyrimidine (precursor 1-7) and the corresponding meta-substituted aniline by boiling in n-butanol:

Example 5: 4-(m-Methylanilino)-5,6-dimethyl-7H-pyrrolo[2,3-d]pyrimidine m.p.: 230°–234° C.;

$C_{15}H_{16}N_4$: FAB-MS (M+H)+=253.

Example 6: 4-(m-Methoxyanilino)-5,6-dimethyl-7H-pyrrolo[2,3-d]pyrimidine m.p.: 209°–214° C.

$C_{15}H_{15}N_4O$: FAB-MS: (M+H)+=269.

In a manner analogous to that described in precursor 1-3, the following compounds are prepared starting from 4-chloro-5,6-tetramethylene-7-benzyl-pyrrolo[2,3-d]pyrimidine (precursor 2—2) by reaction with the corresponding meta-substituted aniline:

Precursor 2-4: 4-(m-Chloroanilino)-5,6-tetramethylene-7-benzyl-pyrrolo[2,3-d]pyrimidine m.p.: 145°–147° C. $C_{23}H_{21}ClN_4$: FAB-MS: (M+H)+=389.

Precursor 2-5: 4-(m-Bromoanilino)-5,6-tetramethylene-7-benzyl-pyrrolo[2,3-d]pyrimidine m.p.: 159°–161° C. $C_{23}H_{21}BrN_4$: FAB-MS: (M+H)+=434.

Precursor 2-6: 4-(m-Fluoroanilino)-5,6-tetramethylene-7-benzyl-pyrrolo[2,3-d]pyrimidine m.p.: 131°–132° C. $C_{23}H_{21}FN_4$: FAB-MS: (M+H)+=373.

The removal of the benzyl-protecting group is effected analogously to Example 1. The following are obtained:

Example 7: 4-(m-Chloroanilino)-5,6-tetramethylene-7H-pyrrolo[2,3-d]pyrimidine m.p.: 246°–249° C. $C_{16}H_{15}ClN_4$: FAB-MS: (M+H)+=299.

Example 8: 4-(m-Bromoanilino)-5,6-tetramethylene-7H-pyrrolo[2,3-d]pyrimidine m.p.: 240°–245° C. $C_{16}H_{15}BrN_4$: FAB-MS: (M+H)+=343.

Example 9: 4-(m-Fluoroanilino)-5,6-tetramethylene-7H-pyrrolo[2,3-d]pyrimidine m.p.:>240° C. $C_{16}H_{15}FN_4$: FAB-MS: (M+H)+=283.

In a manner analogous to that described for precursor 1-3, the following compounds are prepared starting from 4-chloro-5,6-tetramethylene-7H-pyrrolo[2,3-d]pyrimidine (precursor 2-3) and the corresponding meta-substituted aniline by boiling in n-butanol:

Example 10: 4-(m-Methylanilino)-5,6-tetramethylene-7H-pyrrolo[2,3-d]pyrimidine m.p.: 258°–261° C. $C_{17}H_{18}N_4$: FAB-MS: (M+H)+=279.

Example 11: 4-(m-Methoxyanilino)-5,6-tetramethylene-7H-pyrrolo[2,3.d]pyrimidine m.p.: 239°–241° C.

$C_{17}H_{18}N_4O$: FAB-MS: (M+H)+=295.

The following compounds are prepared in an analogous manner from 4-chloro-5,6-diphenyl-7H-pyrrolo[2,3-d]pyrimidine (precursor 3—3):

Example 12: 4-(m-Chloroanilino)-5,6-diphenyl-7H-pyrrolo[2,3-d]pyrimidine m.p.:>270° C.

$C_{24}H_{17}ClN_4$: FAB-MS: (M+H)+=396.

Example 13: 4-(m-Bromoanilino)-5,6-diphenyl-7H-pyrrolo[2,3-d]pyrimidine m.p.:>260° C.

$C_{24}H_{17}BrN_4$: FAB-MS: (M+H)+=441.

Example 14: 4-(m-Trifluoromethylanilino)-5,6-tetramethylene-7H-pyrrolo[2,3-d]-pyrimidine 150 mg (0.85 mmol) of 4-hydroxy-5,6-tetramethylene-7-phenethyl-pyrrolo[2,3-d]-pyrimidine (prepared by ring closure of 2-amino-1-phenethyl-3-cyano-4,5,6,7-tetrahydroindole with 85% formic acid analogously to precursor 1—1) are heated at 240° C. for approximately 5 hours with 483 mg (3.4 mmol) of phosphorus pentoxide, 468 mg (3.4 mmol) of triethylamine hydrochloride and 675 mg (3.4 mmol) of 3-trifluoromethyl-aniline analogously to a known process (see J. Heterocycl. Chem. 22, 859 (1985)). 15 ml of 2N NaOH are then added at 80°–100° C., with stirring. The pasty precipitate is filtered off and the mother liquor is extracted repeatedly with ethyl acetate. The ethyl acetate phase is washed with water, dried and concentrated by evaporation. The precipitate and the ethyl acetate residue are chromatographed together over 60 g of silica gel. Elution with methylene chloride/methanol (95:5) yields 4-(m-trifluoromethylanilino)-5,6-tetra-methylene-7H-pyrrolo[2,3-d]pyrimidine in the form of light-yellow crystals having a melting point of 259°–261° C.

$C_{17}H_{15}F_3N_4$: FAB-MS (M+H)+=333.

The following is prepared analogously to Example 14:

Example 15: 4-(m,n-Dichloroanilino)-5,6-tetramethylene-7H-pyrrolo[2, 3-d]pyrimidine Preparation using m,p-dichloroaniline instead of 3-trifluoromethylaniline; result: title compound m.p.:>270° C.

$C_{16}H_{14}Cl_2N_4$: FAB-MS: (M+H)+=333.

Examples 16 to 22 below relate to the use of compounds of formula I that are already known (see Jorgerisen, A., et al., J. Heterocyclic Chem. 22, 859 (1985)):

The test systems are identified as follows:

Test A) Inhibitory action on EGF-R ICD (ICD=intracellular domains): The test system is described above. The result is given as $IC_{50}$ in µM (concentration of active ingredient at which inhibition is half the maximum inhibition).

Test B) Inhibitory action on the growth of MK cells: The test system is described in detail above. The result is given as $IC_{50}$ in μM (concentration of active ingredient at which inhibition is half the maximum inhibition).

Test C) Inhibitory action on A431 tumour growth in vivo: The test system is described in detail above. The result (as T/C %) and more detailed test conditions are shown in tabular form.

Example 16: 4-Anilino-5,6-dimethyl-7H-pyrrolo[2,3-d]pyrimidine

Test A): 2 μM
Test B): 24.6 μM

Example 17: 4-(p-Methylanilino)-5,6-dimethyl-7H-pyrrolo[2,3-d]pyrimidine

Test A): 1.9 μM
Test B): 24.6 μM

Example 18: 4-(m,p-Dichloroanilino)-5,6-dimethyl-7H-pyrrolo[2,3-d]pyrimidine Test A): 0.070 μM
Test B): 34.8 μM

Example 19: 4-(o-Fluoroanilino)-5,6-dimethyl-7H-pyrrolo[2,3-d]pyrimidine

Test A): 1.6 μM
Test B): 49.3 μM

Example 20: 4-(p-Fluoroanilino)-5,6-dimethyl-7H-pyrrolo[2,3-d]primidine

Test A): 0.56 μM
Test B): 13.1 μM

Example 21: 4 Anilino-5,6-tetramethylene-7H-pyrrolo[2,3-d]primidine

Test A): 0.31 μM
Test B): 12.8 μM

Example 22: 4 (4-Methylanilino)5,6-tetramethylene-7H-pyrrolo[2,3d]pyrimidine Test A): 0.11 μM
Test B): 13.9 μM

Example 23: Dry-fill capsules 5000 capsules are prepared, each comprising as active ingredient 0.25 g of one of the compounds of formula I mentioned in Examples 1 to 22 or 26 to 31:

| Composition: | |
|---|---|
| active ingredient | 1250 g |
| talcum | 180 g |
| wheat starch | 120 g |
| magnesium stearate | 80 g |
| lactose | 20 g |

Preparation process: The powdered substances mentioned are pressed through a sieve having a mesh size of 0.6 mm. 0.33 g portions of the mixture are introduced into gelatin capsules by means of a capsule-filling machine.

Example 24: Soft capsules 5000 soft gelatin capsules, each comprising as active ingredient 0.05 g of one of the compounds of formula I mentioned in Examples 1 to 22 or 26 to 31, are prepared:

| Composition: | |
|---|---|
| active ingredient | 250 g |
| Lauroglykol | 2 l |

Preparation process: The powdered active ingredient is suspended in ®Lauroglykol (propylene glycol laurate, Gattefossé S. A., Saint Priest, France) and ground to a particle size of approximately from 1 to 3 μm in a wet pulveriser. 0.419 g portions of the mixture are then introduced into soft gelatin capsules by means of a capsule-filling machine.

Example 25: Soft capsules 5000 soft gelatin capsules, each comprising as active ingredient 0.05 g of one of the compounds of formula I mentioned in Examples 1 to 22 or 26 to 31, are prepared:

| Composition: | |
|---|---|
| active ingredient | 250 g |
| PEG 400 | 1 l |
| Tween 80 | 1 l |

Preparation process: The powdered active ingredient is suspended in PEG 400 (poly-ethylene glycol with $M_r$ from approximately 380 to approximately 420, Fluka, Switzerland) and ®Tween 80 (polyoxyethylene sorbitan monolaurate, Atlas Chem. Ind., Inc., USA, supplied by Fluka, Switzerland) and is ground to a particle size of approximately from 1 to 3 μm in a wet pulveriser. 0.43 g portions of the mixture are then introduced into soft gelatin capsules by means of a capsule-filling machine.

Precursor 4-1: 2-Amino-3-carboxyethyl-5-(4-methoxyphenyl)-pyrrole 10 ml of abs. ethanol and 1.668 g (10 mmol) of amidinoacetic acid ethyl ester. HCl are placed, under argon, in a dry three-necked flask, the mixture is cooled to 0°–5° C., and 716 mg (10 mmol) of sodium ethanolate (95%) are added. 1.145 g (5 mmol) of 4-methoxyphenacyl bromide (Fluka, Buchs, Switzerland) are then added and the mixture is allowed to warm to RT. Stirring is then carded out for a further 50 h. The reaction mixture is then taken up in an emulsion of water and ethyl acetate. The organic phase is extracted 3 times with water and then once with saturated NaCl solution. The aqueous phases are combined and back-extracted with ethyl acetate. The combined organic phases are dried over magnesium sulfate, filtered and concentrated to dryness by evaporation. The resulting residue is purified by means of flash chromatography on a silica gel 60 column (40 mg; Merck, Darmstadt, Germany), with ethyl acetate/hexane (1:1) being used as eluant. The product fractions are combined, concentrated to dryness by evaporation and stirred with diethyl ether/n-hexane. The product is filtered off with suction and washed with n-hexane. Drying under a high vacuum yields the title compound, m.p. 141°–142° C.; FAB-MS: $(M+H)^+=260$.

(Amidinoacetic acid ethyl ester•HCl is prepared from cyanoacetic acid ethyl ester (Fluka, Buchs, Switzerland) by reaction in HCl and ethanol, stirring the suspension for 22 h, adding ether, stirring for a further 10 min., filtering off, when cold, the resulting crystals of the resulting 3-ethoxy-3-iminopropanoic acid ethyl ester, adding those crystals to ammonia-saturated ethanol and stirring the suspension, filtering the suspension, adding acetone and filtering again;

and adding HCl in diethyl ether to the filtrates, whereupon the amidinoacetic acid ethyl ester•HCl salt precipitates and is then used further).

The following starting materials are prepared analogously to Precursor 4-1:

Precursor 5-1: 2-Amino-3-carboxyethyl-(2,5-dimethoxyphenyl)-pyrrole (Starting materials: amidinoacetic acid ethyl ester•HCl and 2-bromo-2',5'-dimethoxy-acetophenone [Aldrich, Buchs, Switzerland])

Title compound: m.p.: 110°–111° C.; FAB-MS: $(M+H)^+$ =291.

Precursor 6-1: 2-Amino-3-carboxyethyl-5-(phenyl)-pyrrole (Starting materials: amidinoacetic acid ethyl ester•HCl and phenacyl bromide (Aldrich, Buchs, Switzerland))

Title compound: FAB-MS: $(M+H)^+$=231; $^1$H-NMR (DMSO): δ=7.5 (d, 2H); 7.3 (t, 2H); 7.1 (m, 1H); 6.5 (s, 1H); 5.7 (s, 2H); 4.15 (m, 2H); 1.25 (m, 3H).

Precursor 7-1: 2-Amino-3-carboxyethyl-4-methyl-5-(4-methoxyphenyl)-pyrrole (Starting materials: amidinoacetic acid ethyl ester•HCl and 2-bromo-4'-methoxy-propio-phenone [prepared from 4'-methoxypropiophenone {Aldrich, Buchs, Switzerland} by bromination with $Br_2$/$CH_3COOH$, see Chem. Ber. 22, 3251 (1889)])

Title compound: FAB-MS: $(M+H)^+$=275.

Precursor 8-1: 2-Amino-3-carboxyethyl-5-(3-methoxyphenyl)-pyrrole (Starting materials: amidinoacetic acid ethyl ester•HCl and 3-methoxyphenacyl bromide (Aldrich, Buchs, Switzerland))

Title compound: m.p.: 96°–97° C.; $^1$H-NMR (DMSO): δ=7.2 (m, 1H); 7.05 (m, 2H); 6.65 (m, 1H); 6.5 (m, 1H); 5.7 ($NH_2$); 4.13 (q, 2H); 3.86 (s, 3H); 1.23 (t, 3H).

Precursor 9-1: 2-Amino-3-carboxyethyl-5-(2-methoxyphenyl)-pyrrole (Starting materials: amidinoacetic acid ethyl ester·HCl and 2-methoxyphenacyl bromide (Aldrich, Buchs, Switzerland))

Title compound: m.p.: 128° C.; $^1$H-NMR (DMSO): δ=10.3 (1H); 7.45 (m, 1H); 6.8-7.2 (m, 3H); 6.53 (m, 1H); 5.7 ($NH_2$); 4.15 (q, 2H); 3.86 (s, 3H); 1.25 (t, 3H).

Precursor 4-2: 4-Hydroxy-6-(4-methoxyphenyl)-7H-pyrrolo[2,3-d]pyrimidine 610.7 mg (2.5 mmol) of 2-amino-3-carboxyethyl-5-(4-methoxyphenyl)-pyrrole (precursor 4-1), 5 ml of formamide, 2.5 ml of N,N-dimethylformamide and 1.25 ml of formic acid are stirred together at 150° C. for 16 hours. A small amount of isopropanol is added to the warm reaction mixture. After cooling the reaction mixture, the resulting product is filtered off and washed with a small amount of isopropanol and twice with 10 ml of hexane each time. Drying under a high vacuum yields the title compound in the form of light-beige crystals; m.p. >300° C., $^1$H-NMR (DMSO): δ=7.87 (1H); 7.80 (1H); 7.16 (1H); 7.02–6.95 (2H); 6.8 (1H); 3.8 (3H); FAB-MS: $(M+H)^+$=242.

The following title compounds of precursors 5-2 to 9-2 are prepared in an analogous manner from the title compounds of precursors 5-1 to 9-1:

Precursor 5-2: 4-Hydroxy-6-(2,5-dimethoxyphenyl)-7H-pyrrolo[2,3-d]pyrimidine

The title compound is obtained from precursor 5-1: m.p.: >300° C.; FAB-MS: $(M+H)^+$=272.

Precursor 6-2: 4-Hydroxy-6-([4-]-phenyl)-7H-pyrrolo[2,3-d]pyrimidine

The title compound is obtained from precursor 6-1: m.p.: >300° C.; FAB-MS: $(M+H)^+$=212.

Precursor 7-2: 4-Hydroxy-5-methyl-6-(4-methoxyphenyl)-7H-pyrrolo[2,3-d]pyrimidine The title compound is obtained from precursor 7-1: FAB-MS: $(M+H)^+$=256.

Precursor 8-2: 4-Hydroxy-6-(3-methoxyphenyl)-7H-pyrrolo[2,3-d]pyrimidine

The title compound is obtained from precursor 8-1: m.p.: >300° C.; $^1$H-NMR (DMSO): δ=7.9 (1H); 7.28–7.46 (m, 3H); 6.98 (s, 1H); 6.85 (m, 1H); 3.83 (s, 3H).

Precursor 9-2: 4-Hydroxy-6-(2-methoxyphenyl)-7H-pyrrolo[2,3-d]pyrimidine

The title compound is obtained from precursor 9-1: m.p.: >300° C.; $^1$H-NMR (DMSO): δ=12 (1H); 7.9 (1H), 7.77 (m, 1H); 6.95–7.4 (m, 4H); 3.95 (3H).

The title compounds of precursors 4-2 to 9-2 are then reacted analogously to precursor 1-2 with $POCl_3$ to yield the following precursors 4-3 to 9-3:

Precursor 4-3: 4-Chloro-6-(4-methoxyphenyl)-7H-pyrrolo[2,3-d]pyrimidine The title compound is obtained from precursor 4-2: m.p.: 248°–249° C.; FAB-MS: $(M+H)^+$=260.

Precursor 5-3: 4-Chloro-6-(2,5-dimethoxyphenyl)-7H-pyrrolo[2,3-d]pyrimidine

The title compound is obtained from precursor 5-2: $^1$H-NMR (DMSO): δ=8.6 (s, 1H); 7.5 (d, 1H); 7.15 (d, 1H); 7.1 (s, 1H); 7.0 (m, 1H); 3.9 (s, 3H); 3.8 (s, 3H).

Precursor 6-3: 4-Chloro-6-(phenyl)-7H-pyrrolo[2,3-d]pyrimidine

The title compound is obtained from precursor 6-2: FAB-MS: $(M+H)^+$=230; $^1$H-NMR (DMSO): δ=8.6 (s, 1H); 8.05 (d, 2H); 7.5 (m, 3H); 7.1 (s, 1H).

Precursor 7-3: 4-Chloro-5-methyl-6-(4-methoxyphenyl)-7H-pyrrolo[2,3-d]pyrimidine The title compound is obtained from precursor 7-2: FAB-MS: $(M+H)^+$=274.

Precursor 8-3: 4-Chloro-6-(3-methoxyphenyl)-7H-pyrrolo[2,3-d]pyrimidine

The title compound is obtained from precursor 8-2: (it is not isolated, but is used further in the form of the crude product).

Precursor 9-3: 4-Chloro-6-(2-methoxyphenyl)-7H-pyrrolo[2,3-d]pyrimidine

The title compound is obtained from precursor 9-2: (it is not isolated, but is used further in the form of the crude product).

Analogously to precursor 1-3, the title compounds from each of precursors 5-3, 6-3, 7-3, 8-3 and 9-3 are reacted with m-chloroaniline to yield the following Examples (=4-(m-chloroanilino)-7H-pyrrolo[2,3-d]pyrimidines):

Example 26: 4-(m-Chloroanilino)-6-(4-methoxyphenyl)-7H-pyrrolo[2,3-d]pyrimidine

The title compound is obtained from precursor 4-3: m.p.: 294–295° C.; FAB-MS: $(M+H)^+$=351.

Example 27: 4-(m-Chloroanilino)-6-(2,5-dimethoxyphenyl)-7H-pyrrolo[2,3-d]-pyrimidine The title compound is obtained from precursor 5-3: m.p.: 267°–268° C.; FAB-MS: $(M+H)^+$=381.

Example 28: 4-(m-Chloroanilino)-6-(phenyl)-7H-pyrrolo[2,3-d]pyrimidine

The title compound is obtained from precursor 6-3: m.p.: 285°–286° C.; FAB-MS: $(M+H)^+$=321.

Example 29: 4-(m-Chloroanilino)-5-methyl-6-(4-methoxyphenyl)-7H-pyrrolo[2,3-d]-pyrimidine The title compound is obtained from precursor 7-3: FAB-MS: $(M+H)^+$=365.

Example 30: 4-(m-Chloroanilino)-6-(3-methoxyphenyl)-7H-pyrrolo[2,3-d]pyrimidine The title compound is obtained from precursor 8-3: m.p.: 262°–263° C.; FAB-MS: (M+H)$^+$=351.

Example 31: 4-(m-Chloroanilino)-6-(2-methoxyphenyl)-7H-pyrrolo[2,3-d]pyrimidine The title compound is obtained from precursor 9-3: m.p.: 221°–222 C.; FAB-MS: (M+H)$^+$=351.

Example 32: Inhibitory action on the intracellular domains of EGF-R (ICD)

The test system is described above. The result is given as $IC_{50}$ in µM (concentration of active ingredient at which inhibition is half the maximum inhibition).

| Compound of Example | $IC_{50}$ |
|---|---|
| 1 | 0.045 |
| 2 | 0.025 |
| 3 | 0.55 |
| 4 | 0.17 |
| 5 | 0.57 |
| 6 | 1.2 |
| 7 | 0.033 |
| 8 | 0.046 |
| 9 | 0.2 |
| 10 | 0.82 |
| 11 | 0.35 |
| 12 | 0.096 |
| 13 | 0.033 |
| 14 | 0.36 |
| 15 | 0.15 |
| 26 | 0.015 |
| 27 | 0.033 |
| 28 | 0.013 |
| 29 | 0.43 |
| 30 | 1.77 |
| 31 | 0.019 |

Example 33: Inhibitory action on A431 tumour growth in vivo

The test system is described in detail above. The result (as T/C %) and more detailed test conditions are shown in tabular form:

Animals: Female Balb/c nu/nu nude mice (Tif/Si or Bomholtgard)

Formulation: Dimethyl sulfoxide/®Tween 80/0.9% NaCl.

| Compound of Ex. | Administration | Dose (mg/kg) | T/C % Exp. 1 | Exp. 2 | Exp. 3 |
|---|---|---|---|---|---|
| 1 | p.o. | 125 | — | 2 | — |
|  | p.o. | 50 | 14 | 9 | 14 |
|  | p.o. | 25 | 16 | 14 | 16 |
|  | p.o. | 12.5 | — | 16 | 21 |
|  | p.o. | 6.25 | — | 23 | 32 |
|  | p.o. | 3.13 | — | 29 | 41 |
|  | p.o. | 1.56 | — | 45 | 61 |
|  | i.p. | 31.25 | — | 3 | — |
|  | i.p. | 25.00 | — | — | 12 |
|  | i.p. | 12.5 | 11 | 6 | 16 |
|  | i.p. | 6.25 | 11 | 8 | 28 |
|  | i.p. | 3.13 | — | 12 | 22 |
|  | i.p. | 1.56 | — | 21 | 29 |
|  | i.p. | 0.78 | — | 50 | 58 |
|  | i.p. | 0.39 | — | 58 | — |

Treatment begins on day 5 (Exp. 1), day 7 (Exp. 2) or day 6 (Exp. 3) after transplantation of the tumour and is then carried out once daily for 15 days.

| Compound | Administration | Dose (mg/kg) | T/C % |
|---|---|---|---|
| none (control) | — | — | 100 |
| of Ex. 7 | daily from day 6 to day 20 | | |
|  | p.o. | 50.00 | 17 |
|  | p.o. | 25.00 | 28 |
|  | p.o. | 12.50 | 45 |
|  | p.o. | 6.25 | 55 |
|  | p.o. | 3.13 | 68 |
|  | p.o. | 1.56 | 84 |
|  | i.p. | 50.00 | 12 |
|  | i.p. | 25.00 | 15 |
|  | i.p. | 12.50 | 18 |
|  | i.p. | 6.25 | 41 |
|  | i.p. | 3.13 | 61 |
|  | i.p. | 1.56 | 88 |

Note:
After i.p. administration (60 - 6.25 mg/kg), some of the compound is not absorbed

| Compound of Ex. | Administration | Dose (mg/kg) | T/C % Exp. 1 | Exp. 2 |
|---|---|---|---|---|
| 26 | daily from day 6 to day 20 | | | |
|  | i.p. | 50 | 15 | 15 |
|  | i.p. | 12.5 | 32 | 57 |
|  | i.p. | 3.13 | 35 | 84 |

What is claimed is:

1. A method for the therapeutic treatment of a tumour disease or psoriasis in a warm-blooded animal requiring such treatment, in which a composition comprising as active ingredient 4-(m-chloroanilino)-5,6-dimethyl-7H-pyrrolo[2,3-d]pyrimidine, or a pharmaceutically acceptable salt thereof, is administered to said warm-blooded animal in an amount that is effective against said disease.

2. A pharmaceutical composition for the therapeutic treatment of a tumour disease or psoriasis in a warm-blooded animal requiring such treatment, which composition comprises as active ingredient 4-(m-chloroanilino)-5,6-dimethyl-7H-pyrrolo[2, 3-d]pyrimidine, or a pharmaceutically acceptable salt thereof, in an amount that is therapeutically effective against said disease.

* * * * *